(12) United States Patent
Cheng et al.

(10) Patent No.: US 9,062,081 B1
(45) Date of Patent: Jun. 23, 2015

(54) PREPARATION OF PHENOL- OR THIOPHENYL-SULFONIC ACID FUNCTIONALIZED SOLID ACIDS

(71) Applicant: National Taiwan University, Taipei (TW)

(72) Inventors: Soofin Cheng, Taipei (TW); Chia-Han Chen, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 14/139,961

(22) Filed: Dec. 24, 2013

(51) Int. Cl.
*C07F 7/18* (2006.01)

(52) U.S. Cl.
CPC .................................. *C07F 7/1892* (2013.01)

(58) Field of Classification Search
CPC ........................................................ C07F 7/18
USPC ....................................... 549/4; 556/400, 449
See application file for complete search history.

(56) References Cited

U.S. PATENT DOCUMENTS

| 3,931,267 | A  | * | 1/1976  | Brode ............................ 556/449 |
| 4,439,494 | A  | * | 3/1984  | Olson ............................ 428/412 |
| 7,815,883 | B2 | * | 10/2010 | Cheng et al. .................... 423/335 |
| 8,624,035 | B2 | * | 1/2014  | Caputo et al. ................... 548/110 |

* cited by examiner

*Primary Examiner* — Golam M M Shameem
(74) *Attorney, Agent, or Firm* — McClure, Qualey & Rodack, LLP

(57) ABSTRACT

Some aryl sulfonic acid-functionalized solids were prepared by a new method. The catalytic activities of esterification by the prepared aryl sulfonic acid-functionalized solids were also tested.

6 Claims, 13 Drawing Sheets

PREPARATION OF PHENOL- OR THIOPHENYL-SULFONIC ACID FUNCTIONALIZED SOLID ACIDS

BACKGROUND

1. Technical Field

The disclosure relates to preparation of solid acids.

2. Description of Related Art

Solid acids are widely used in industry. There are two important types of solid acids, one is acid aluminosilicate zeolite, and the other one is acid resin (such as amberlyst-15 having a polystyrene backbone). However, the pore size of the acid aluminosilicate zeolite is too small to accommodate large medical molecules, and the reaction temperature needed by the acid aluminosilicate zeolite is usually 200-300° C. to present enough acidity. As for the acid resin, the acid resin will be swelled by solvents to affect the effective acid amount, and the thermal stability of the acid resin is kind of poor. Therefore, the acid resin is usually deteriorated after reaction and difficult to be regenerated.

SUMMARY

In one aspect, the present disclosure provides a method of preparing an aryl sulfonic acid-functionalized solid to be a solid acid. The method comprises the following steps. First, a 3-arylpropyl trimethoxysilane is formed by reacting 3-chloropropyl trimethoxysilane with an aromatic compound. Then, an aryl-functionalized solid is formed by grafting the 3-arylpropyl trimethoxysilane onto an inorganic solid material in an organic solvent under a reflux condition. Next, an aryl sulfonic acid-functionalized solid is formed by sulfonating the aryl-functionalized solid by a sulfonating agent.

According to an embodiment, the aromatic compound is phenol, alkyl phenol, thiophene, or alkyl thiophene.

According to another embodiment, the inorganic solid material is silica gel or $Zr(OH)_4$ powders.

According to yet another embodiment, the organic solvent is toluene, xylene, ethylbenzene, or octane.

According to yet another embodiment, the aryl-functionalized solid is sulfonated at 60-90° C. for 6-36 hours.

According to yet another embodiment, the sulfonating agent is concentrated sulfuric acid, a mixture of oleum and concentrated sulfuric acid, or $SO_2Cl_2$.

In another aspect, the present disclosure provides a method of preparing an aryl sulfonic acid-functionalized solid to be a solid acid. The method comprises the following steps. First, a 3-arylpropyl trimethoxysilane is formed by reacting 3-chloropropyl trimethoxysilane with an aromatic compound. Then, an aryl-functionalized solid is formed by co-condensing the 3-arylpropyl trimethoxysilane and a precursor of an inorganic solid by a hydrothermal reaction. Next, an aryl sulfonic acid-functionalized solid is formed by sulfonating the aryl-functionalized solid in concentrated sulfuric acid.

According to an embodiment, the precursor of the inorganic solid is tetramethyl orthosilicate, tetraethyl orthosilicate, or sodium silicate.

According to another embodiment, the inorganic solid comprises a porous silica material.

According to yet another embodiment, the porous silica material is SBA-15 or MCM41.

According to yet another embodiment, a reactant composition of the hydrothermal reaction comprises a pore directing agent, the precursor of the inorganic solid, an acid, and water in a molar ratio of 0.02:1:0.05-0.3:7-9:179-230.

According to yet another embodiment, the pore directing agent is $EO_{20}PO_{70}EO_{20}$, $EO_{40}PO_{60}EO_{40}$, $EO_{100}PO_{65}EO_{100}$, or cetyl trimethylammonium bromide.

According to yet another embodiment, the acid is HCl, $HNO_3$, $H_2SO_4$, or $HClO_4$.

According to yet another embodiment, the reactant composition of the hydrothermal reaction further comprises Zr(IV) ions, and atomic ratio of Zr(IV):Si is in 0-0.1.

According to yet another embodiment, a source of the Zr(IV) ions is $ZrOCl_2$, $ZrSO_4$, $ZrO(NO_3)_2$, or zirconium(IV) acetate hydroxide.

According to yet another embodiment, a reactant composition of the hydrothermal reaction comprises 0.017 $EO_{20}PO_{70}EO_{20}$:1 tetraethyl orthosilicate:0.05-0.43 3-arylpropyl trimethoxysilane:0.05 $ZrOCl_2 \cdot 8H_2O$:7.9 HCl:220 $H_2O$ in molar ratio.

According to yet another embodiment, the aryl-functionalized solid is sulfonated at 60-90° C. for 6-36 hours.

According to yet another embodiment, the sulfonating agent is concentrated sulfuric acid, a mixture of oleum and concentrated sulfuric acid, or $SO_2Cl_2$.

The foregoing presents a simplified summary of the disclosure in order to provide a basic understanding to the reader. This summary is not an extensive overview of the disclosure and it does not identify key/critical elements of the present disclosure or delineate the scope of the present disclosure. Its sole purpose is to present some concepts disclosed herein in a simplified form as a prelude to the more detailed description that is presented later. Many of the attendant features will be more readily appreciated as the same becomes better understood by reference to the following detailed description considered in connection with the accompanying drawings.

DETAILED DESCRIPTION

Figure 1:
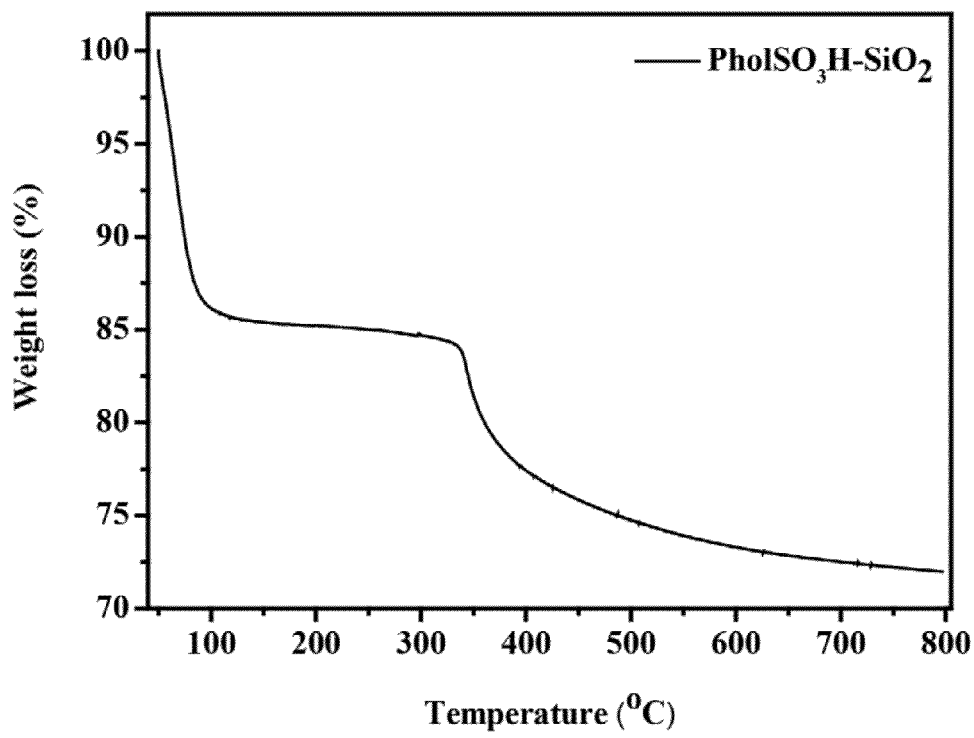
FIG. 1 is the TGA profile of $PholSO_3H$—$SiO_2$.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

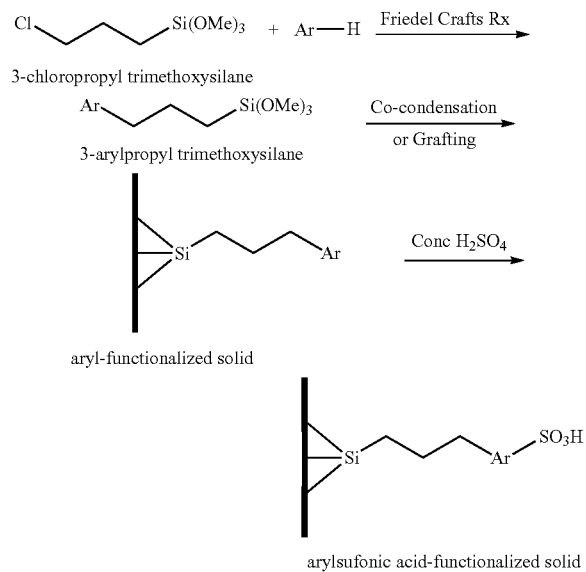

Scheme 1

In scheme 1, 3-chloropropyl trimethoxysilane was used as a starting material to perform a Friedel-Crafts reaction with an aromatic compound, such as phenol, alkyl phenol, thiophene, or alkyl thiophene, to obtain 3-arylpropyl trimethoxysilane.

Next, the 3-arylpropyl trimethoxysilane can be used to functionalize an inorganic solid material, such as a silica material, a zirconia material, a titania material, or other metal oxide materials, to obtain an aryl-functionalized solid. The silica material above can be silica gel or a porous silica material. This step can be performed by a grafting method or a co-condensation method.

In the grafting method, an inorganic solid material having free —OH functional groups on its surface is needed. The 3-arylpropyl trimethoxysilane above is used to react with the —OH group of the inorganic solid material in an organic solvent under a reflux condition for 1-48 hours, such as at least 24 hours. The solid material can be silica gel or Zr(OH)$_4$ powder. The Zr(OH)$_4$ powder is a precursor of zirconia powder. The organic solvent can be an anhydrous organic solvent with boiling points higher than 80° C., such as toluene, xylene, ethylbenzene, or octane, for example.

In the co-condensation method, 3-arylpropyl trimethoxysilane and a precursor of an inorganic solid is co-condensed in an aqueous solution containing a pore-directing agent to form an aryl-functionalized solid by hydrothermal reaction. The inorganic solid can be a porous silica material, such as SBA-15 or MCM41, for example. The precursor of an inorganic solid may be a silica source.

In a typical method of preparing an aryl-functionalized porous silica material, a pore directing agent, a silica source, acid, and water are needed for the hydrothermal reaction. The molar ratio of the pore directing agent, the silica source, the 3-arylpropyl trimethoxysilane, the acid, and water can be 0.02:1:0.05-0.45:3:7-9:179-230, for example. The pore directing agent can be EO$_{20}$PO$_{70}$EO$_{20}$, EO$_{40}$PO$_{60}$EO$_{40}$, EO$_{100}$PO$_{65}$EO$_{100}$, or cetyl trimethylammonium bromide, for example. The silica source can be tetramethyl orthosilicate (TMOS), tetraethyl orthosilicate (TEOS), or sodium silicate, for example. The acid can be HCl, HNO$_3$, H$_2$SO$_4$, or HClO$_4$, for example. The hydrothermal reaction is usually performed at a temperature of 90-100° C. under static condition for 6-72 hours, such as at least 24 hours.

For synthesizing above-mentioned SBA-15 with short channeling pores, a neutral pore directing agent and Zr(IV) ions are used. The neutral pore directing agent can be EO$_{20}$PO$_{70}$EO$_{20}$, EO$_{40}$PO$_{60}$EO$_{40}$, EO$_{100}$PO$_{65}$EO$_{100}$. The source of the Zr(IV) ions can be ZrOCl$_2$, ZrSO$_4$, ZrO(NO$_3$)$_2$, or zirconium(IV) acetate hydroxide. The atomic ratio of Zr(IV) to Si of the silica source is in 0-0.1, such as 0.05.

Finally, the aromatic ring of the aryl-functionalized solid is sulfonated by a sulfonating agent to obtain an aryl sulfonic acid-functionalized solid as a solid acid. The sulfonating agent can be concentrated sulfuric acid, a mixture of oleum and concentrated sulfuric acid, or SO$_2$Cl$_2$. The sulfonation can be performed at 60-90° C. for 6-36 hours.

Some working examples are described below.

Preparation of 3-Arylpropyl Trimethoxysilane

First, two 3-arylpropyl trimethoxysilanes were synthesized as examples. One was 3-(2-hydroxy-5-methylphenyl)-propyltrimethoxysilane, and the other was 3-thienyl-propyl-trimethoxysilane.

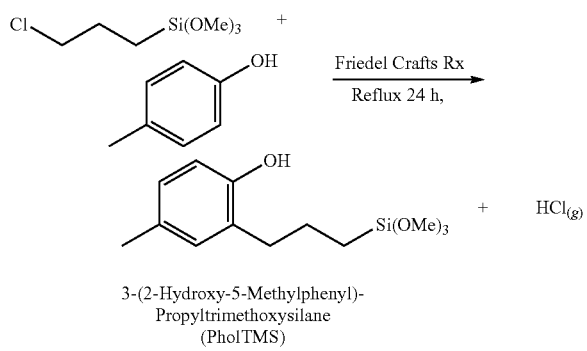

Scheme 2

3-(2-Hydroxy-5-Methylphenyl)-
Propyltrimethoxysilane
(PholTMS)

As shown in Scheme 2, a new 3-arylpropyl trimethoxysilane compound, 3-(2-hydroxy-5-methylphenyl)-propyltrimethoxysilane (abbreviated PholTMS) was synthesized. 60 g of p-cresol and 100 g of 3-chloropropyltrimethoxysilane were mixed under reflux for 24 hours. The product was confirmed by NMR spectrum, and the yield was more than 99%.

$^1$H NMR of PholTMS (400 MHz, CD$_3$OD): δ0.65 (t, 2H), 1.56 (p, 2H), 2.34 (s, 3H), 2.63 (t, 2H), 3.58 (s, 9H), 6.5-7 (m, 3H).

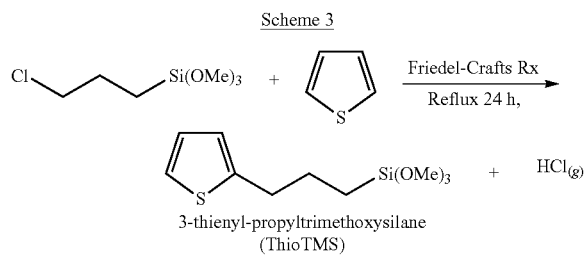

Scheme 3

3-thienyl-propyltrimethoxysilane (ThioTMS)

As shown in Scheme 3, a new 3-arylpropyl trimethoxysilane compound, 3-thienyl-propyltrimethoxysilane (abbreviated ThioTMS) was synthesized. 60 g of thiophene, 100 g of 3-chloropropyltrimethoxysilane and 0.1 g of anhydrous AlCl$_3$ were mixed under reflux for 24 hours. The product was confirmed by NMR spectrum, and the yield was more than 99%. $^1$H NMR of ThioTMS (400 MHz, CD$_3$OD): δ0.65 (t, 2H), 1.56 (p, 2H), 2.66 (t, 2H), 3.58 (s, 9H), 6.5-7 (m, 2H), 7.35 (d, 1H).

Preparation of Aryl Sulfonic Acid-Functionalized Solid by Grafting Method

Example 3

Phenolsulfonic Acid-Functionalized Silica Gel

In this embodiment, PholTMS was grafted onto silica gel to form phenol-functionalized silica gel, which is denoted by Phol-SiO$_2$. Then, phenol-functionalized silica gel was sulfonated by concentrated H$_2$SO$_4$ to form phenolsulfonic acid-functionalized silica gel, which is denoted by PholSO$_3$H—SiO$_2$.

Accordingly, a phenol-functionalized silica gel was prepared first. In this step, 2.0 mL of PholTMS synthesized above was reacted with 4 g of silica gel (Sigma Aldrich) in 10 mL of toluene under reflux for 24 hours. Then, the obtained solid product Phol-SiO$_2$ was filtered and dried at 100° C.

Next, a phenolsulfonic acid-functionalized silica gel was prepared. In this step, 4 g of Phol-SiO$_2$ powder in 40 mL of concentrated H$_2$SO$_4$ was heated at 80° C. for 24 hours. After cooling and diluting the mixture with 150 mL of water, the solid product PholSO$_3$H—SiO$_2$ was collected by filtration and dried at 100° C.

Some physicochemical properties of pristine silica gel and PholSO$_3$H—SiO$_2$ were analyzed. The analyzed physicochemical properties included sulfur content, acid capacity, specific surface area ($S_{BET}$), pore volume ($V_{Total}$), pore diameter ($\phi_P$), and thermogravimetric analysis (TGA).

Nitrogen physisorption isotherms were used to analyze specific surface area ($S_{BET}$), pore volume ($V_{Total}$), pore diameter ($\phi_P$) of the samples. The Nitrogen physisorption isotherms were taken at liquid nitrogen temperature (77 K) by using a Micrometerics TriStar 3000 system. Prior to the experiments, the samples were outgassed at 120° C. for 6-8 h under vacuum (10$^{-3}$ Torr).

The acid capacities of the samples were determined by acid-base titration using NaCl solution as an ion-exchange agent. A 50 mg sample in powder form was ion-exchanged with 20 mL 2M NaCl solution at ambient temperature for at least 24 h, followed by filtration and washing with 3 mL of deionized water. The filtrates were then titrated with a 0.01 M NaOH solution.

The obtained data are shown in Table 1 and FIG. 1. In Table 1, the acid capacity of PholSO$_3$H—SiO$_2$ was close to the sulfur content, and both are around 1 mmol/g. FIG. 1 is the TGA profile of PholSO$_3$H—SiO$_2$. Before 100° C., about 15% weight loss of adsorbed moisture was desorbed. This result shows that the PholSO$_3$H—SiO$_2$ was hygroscopic. Above 340° C., the weight loss was attributed to the decomposition of phenol and sulfonic acid groups.

TABLE 1

Some physicochemical properties of pristine silica gel and PholSO$_3$H—SiO$_2$

| Sample | S Content[a] (mmol/g) | Acid Capacity[b] (mmol H$^+$/g) | $S_{BET}$[c] (m$^2$/g) | $V_{Total}$[d] (cm$^3$/g) | $\phi_P$[e] (nm) |
|---|---|---|---|---|---|
| Silica gel | 0 | — | 600 | — | — |
| PholSO$_3$H—SiO$_2$ | 0.995 | 0.965 | 157 | 0.15 | 18.5 |

[a]Determined by HCS elemental analysis using a Heraeus VarioEL analyzer
[b]Determined by acid-base titration
[c]Calculated by Brunauer-Emmett-Teller (BET) method in the P/P$_0$ range around 0.05-0.25
[d]Determined by Barrett-Joyner-Halenda (BJH) method using the N$_2$ desorption isotherms
[e]Determined by Barrett-Joyner-Halenda (BJH) method using the N$_2$ desorption isotherms Example 4

Phenolsulfonic Acid-Functionalized Zirconia

In this embodiment, PholTMS was grafted onto a zirconia source, such as Zr(OH)$_4$, to form phenol-functionalized zirconia, which is denoted by Phol-ZrO$_2$. Then, phenol-functionalized zirconia was sulfonated by a mixture of concentrated H$_2$SO$_4$ and oleum to form phenolsulfonic acid-functionalized zirconia, which is denoted by PholSO$_3$H—ZrO$_2$.

Accordingly, phenol-functionalized zirconia was prepared first. The preparation of phenol-functionalized zirconia was performed by grafting PholTMS onto the surface of Zr(OH)$_4$ powder, which is a precursor of zirconia. In the preparation of phenol-functionalized zirconia, 1 g of PholTMS was reacted with 1 g of Zr(OH)$_4$ powder in 20 mL toluene solvent under reflux for 24 h. The solid product Phol-ZrO$_2$ was collected by filtration and drying at 100° C.

Next, phenolsulfonic acid-functionalized zirconia was prepared. 1 g of Phol-ZrO$_2$ powders with a mixture of 5 mL oleum (i.e. fuming sulfuric acid) and 20 mL concentrated H$_2$SO$_4$ were heated at 80° C. for 24 h. After cooling and diluting the mixture with 1 L of deionized water, the solid product PholSO$_3$H—ZrO$_2$ was filtered and dried at 100° C.

For comparison, sulfonic acid-functionalized zirconia (denoted by SO$_3$H—ZrO$_2$) was also prepared. 1 g of Zr(OH)$_4$ was reacted directly with a mixture of 5 mL oleum and 20 mL concentrated H$_2$SO$_4$ at 80° C. for 10 hours. After cooling and diluting the mixture with 1 L of deionized water, the solid product was filtered, dried at 200° C. for 10 h.

Figure 2:
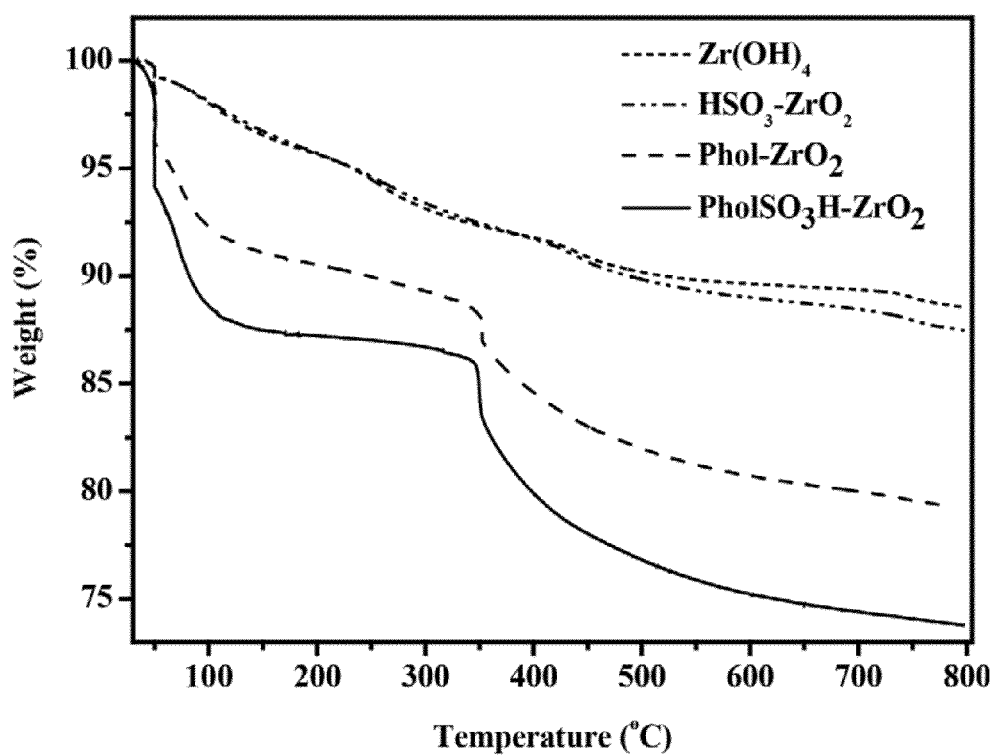
FIG. 2 shows the TGA profiles of the $ZrO_2$ materials before and after functionalized with sulfonic acid, phenol and phenolsulfonic acid groups.

FIG. 2 shows the TGA profiles of the ZrO$_2$ materials before and after functionalized with sulfonic acid, phenol and phenolsulfonic acid groups, respectively. The materials functionalized with phenol (Phol-ZrO$_2$) and phenolsulfonic acid groups (PholSO$_3$H—ZrO$_2$) are more hygroscopic because they adsorb larger amounts of moisture, which was desorbed below 100° C. Moreover, these two samples of Phol-ZrO$_2$ and PholSO$_3$H—ZrO$_2$ have additional weight losses at ca. 350° C. It should correspond to the decomposition of phenol groups.

Preparation of Aryl Sulfonic Acid-Functionalized Solid by Co-Condensation Method

Example 5

Phenolsulfonic Acid-Functionalized SBA-15

SBA-15 is a mesoporous silica material. In this embodiment, PholTMS was co-condensed with a silica source to form phenol-functionalized platelet SBA-15, which is denoted by Phol-SBA-15-p. Then, phenol-functionalized platelet SBA-15 was sulfonated by concentrated H$_2$SO$_4$ to form phenolsulfonic acid-functionalized platelet SBA-15, which is denoted by PholSO$_3$H-SBA-15-p.

Accordingly, phenol-functionalized SBA-15 was prepared first. The preparation of phenol-functionalized SBA-15 was performed by co-condensing a silica source, such as tetraethyl orthosilicate (TEOS), and PholTMS in the presence of Zr(IV) ions.

In a typical synthesis procedure of phenol-functionalized SBA-15, 2.0 g of pore-directing agent such as EO$_{20}$PO$_{70}$EO$_{20}$ (Aldrich, Pluronic P123, Mn=5800) and 0.33 g of zirconyl chloride octahydrate (ZrOCl$_2$.8H$_2$O, Acros) were dissolved in 80 g of 2.0 M HCl (Acros) aqueous solution at 35° C. To this solution, 4.2 g of TEOS (Acros) was added and hydrolyzed for 2 hours before the addition of various amounts of PholTMS. It should be noticed that TEOS prehydrolysis in the acidic synthesis solution containing Zr(IV) ions before the introduction of PholTMS was necessary in order to obtain a well-ordered pore structure and platelet morphology. The reactant compositions were 0.017 P123:1 TEOS:0.05-0.45 PholTMS:0.05 ZrOCl$_2$.8H$_2$O:7.9 HCl:220 H$_2$O, in molar ratio.

The synthesized gel sealed in a polypropylene bottle was stirred at 35° C. for 24 h and hydrothermally heated under static conditions at 90° C. for another 24 h. A solid precipitate collected by filtration was washed thoroughly with deionized water, followed by drying at 50° C. overnight. P123 was removed from the solid materials by ethanol extraction at 78° C. for 1 day. The resulting phenol-functionalized SBA-15 are designated as xPhol-SBA-15-p, where "x" represents the PholTMS/(TEOS+PholTMS) molar percentage in the synthesis gels and "p" indicates the platelet morphology.

Some physicochemical properties of the resulting xPhol-SBA-15-p solids are shown in Table 2. In Table 2, the BET surface area (S$_{BET}$), pore volume (V$_{Total}$) and pore diameter ($\phi_P$) values decreased with the increase of PholTMS concentration in the synthesis solution. This result indicated that the self-assemble process of pore directing agent P123 and silica precursor was interfered by PholTMS. The maximal amount of phenol groups incorporated in platelet SBA-15 by this co-condensation method is about 1.4 mmol/g.

TABLE 2

Some physicochemical properties of xPhol-SBA-15-p

| Sample | F.G. content[a] (mmol/g) | | S$_{BET}$[d] (m$^2$/g) | V$_{Total}$[e] (cm$^3$/g) | $\phi_P$[f] (nm) |
|---|---|---|---|---|---|
| | gel[b] | solid[c] | | | |
| SBA-15-p | 0 | — | 823 | 0.98 | 7.0 |
| 15Phol-SBA-15-p | 1.05 | 1.012 | 504 | 0.67 | 5.2 |
| 20Phol-SBA-15-p | 1.40 | 1.355 | 475 | 0.46 | 3.6/4.1[g] |

TABLE 2-continued

Some physicochemical properties of xPhol-SBA-15-p

| Sample | F.G. content[a] (mmol/g) | | S$_{BET}$[d] (m$^2$/g) | V$_{Total}$[e] (cm$^3$/g) | $\phi_P$[f] (nm) |
|---|---|---|---|---|---|
| | gel[b] | solid[c] | | | |
| 25Phol-SBA_15-p | 1.75 | 1.421 | 416 | 0.41 | 3.6/4.0[g] |
| 30Phol-SBA-15-p | 2.10 | 1.433 | 377 | 0.40 | 3.5/4.0[g] |

[a]Functional group content
[b]Functional group content in the synthesis gel.
[c]Determined by HC elemental analysis
[d]Calculated by Brunauer-Emmett-Teller (BET) method in the P/P$_0$ range around 0.05-0.25
[e]Determined by Barrett-Joyner-Halenda (BJH) method using the N$_2$ desorption isotherms
[f]Determined by Barrett-Joyner-Halenda (BJH) method using the N$_2$ desorption isotherms
[g]Peak maxima at the pore size distribution profiles Next, phenolsulfonic acid-functionalized platelet SBA-15 was prepared. 4 g of xPhol-SBA-15-p powder in 40 mL concentrated H$_2$SO$_4$ was heated at 80° C. for 24 hours. After cooling and diluting the mixture with 150 mL of water, the solid product was filtered and dried at 100° C. The resultant products, phenolsulfonic acid-functionalized platelet SBA-15, are termed as xPholSO$_3$H-SBA-15-p, where x is 15, 20, 25, or 30.

Some physicochemical properties of the resulting phenolsulfonic acid-functionalized SBA-15 are shown in Table 3. The sulfur contents of xPholSO$_3$H-SBA-15-p materials determined by elemental analysis are close to the phenol content, implying that each phenol group undergoes sulfonation. On the other hand, the BET surface areas of all the sulfonated materials decrease to ca. 330-380 m$^2$/g, V$_{Total}$ values to ca. 0.3 cm$^3$/g and $\phi_p$ values to ca. 3.5 nm. The values are little influenced by the acid loadings.

TABLE 3

Some physicochemical properties of the resulting phenolsulfonic acid-functionalized SBA-15

| Sample | F.G. content (mmol/g)[a] | | S$_{BET}$[d] (m$^2$/g) | V$_{Total}$[e] (cm$^3$/g) | $\phi_P$[f] (nm) |
|---|---|---|---|---|---|
| | Phenol[b] | S Content[c] | | | |
| 15PholSO$_3$H-SBA-15-p | 1.012 | 1.067 | 387 | 0.32 | 3.5 |
| 20PholSO$_3$H-SBA-15-p | 1.355 | 1.380 | 331 | 0.29 | 3.6 |
| 25PholSO$_3$H-SBA-15-p | 1.421 | 1.437 | 340 | 0.32 | 3.6 |
| 30PholSO$_3$H-SBA-15-p | 1.433 | 1.444 | 330 | 0.33 | 3.5 |

Figure 3A:
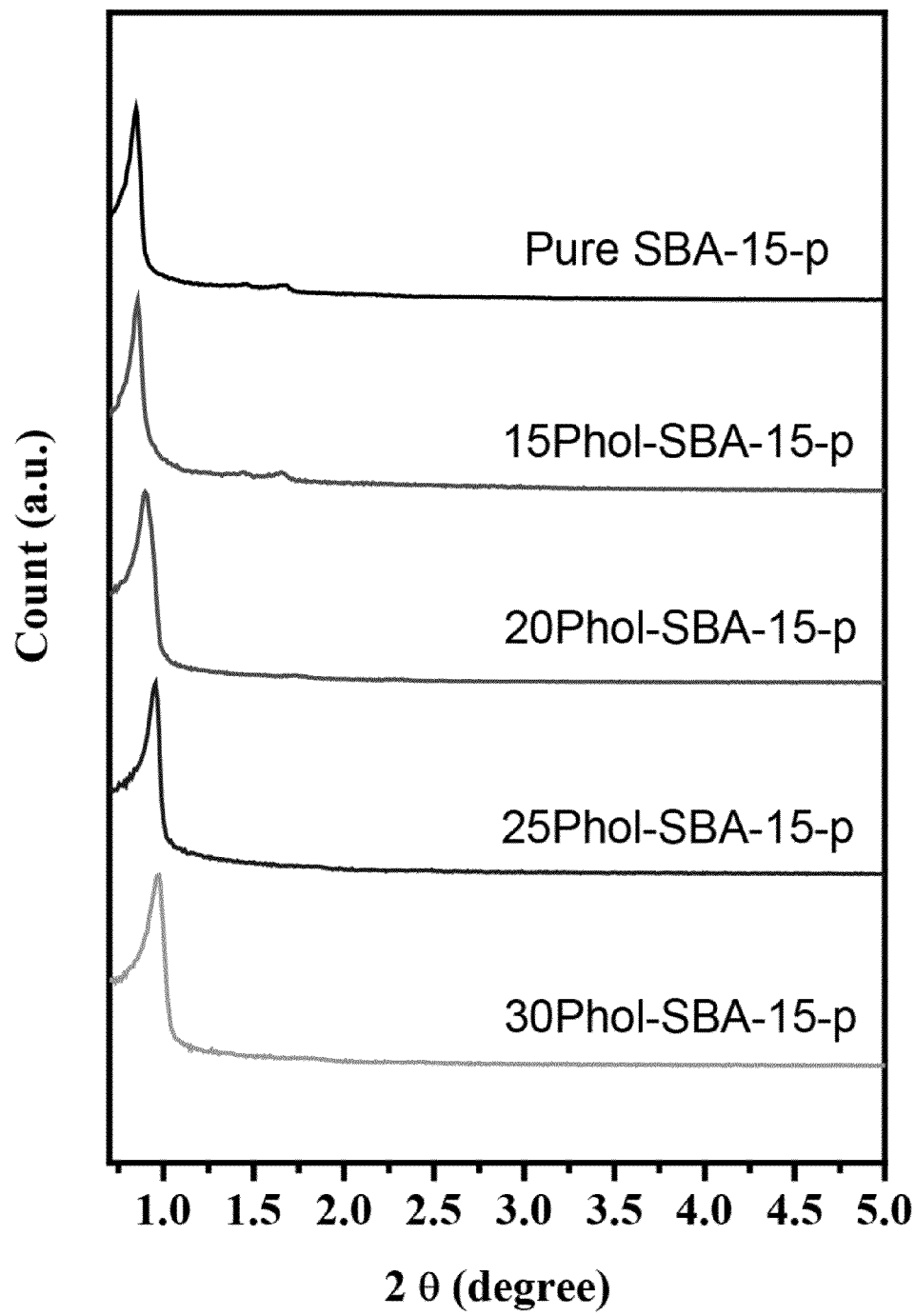
FIGS. 3A and 3B are the small-angle XRD patterns of ethanol extracted xPhol-SBA-15-p and $xPholSO_3H$-SBA-15-p materials prepared with various PholTMS/(TEOS+PholTMS) molar percentages and those after sulfonation, respectively.
Figure 3B:
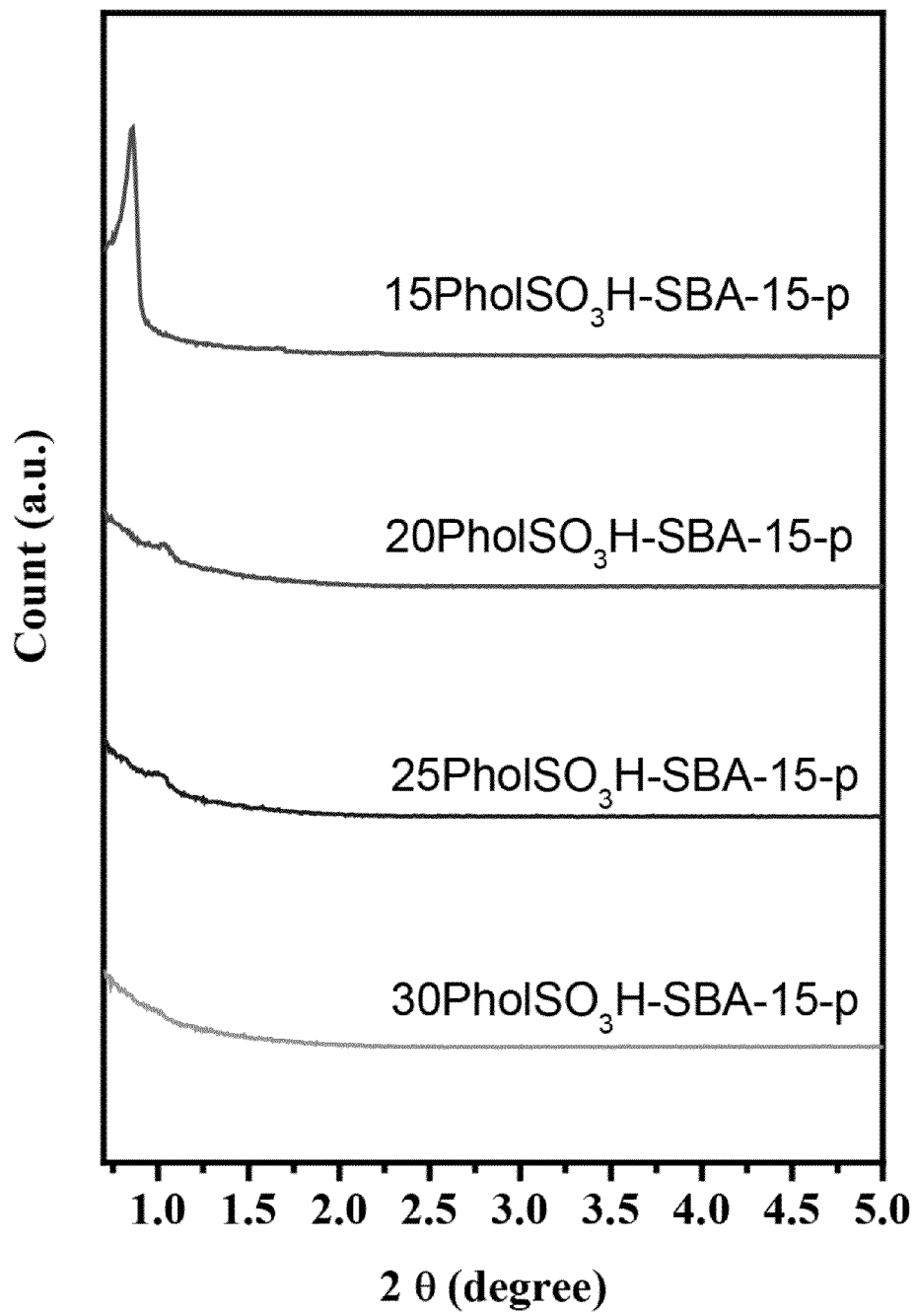
Figure 4A:
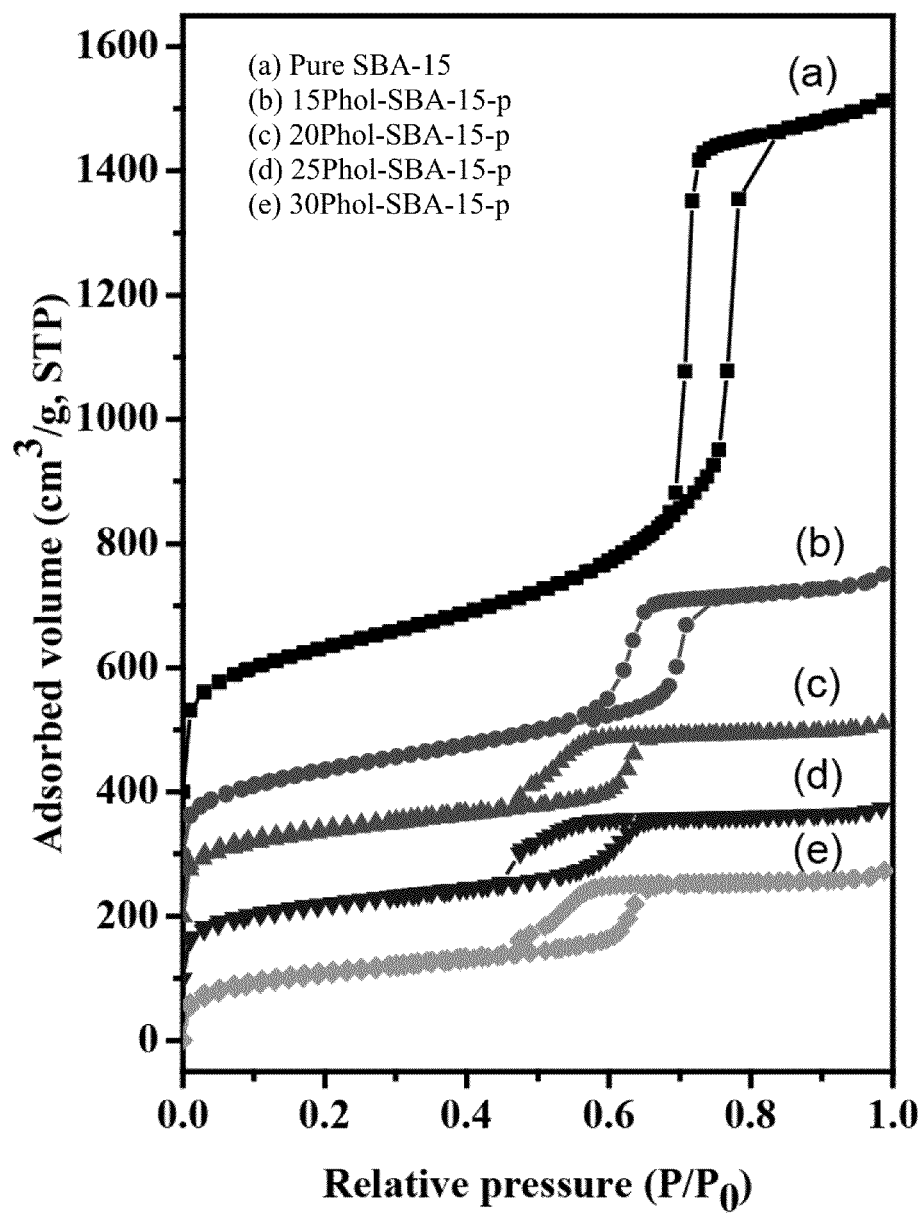
FIGS. 4A and 4B are the nitrogen adsorption-desorption isotherms of ethanol extracted xPhol-SBA-15-p and $xPholSO_3H$-SBA-15-p materials prepared with various PholTMS/(TEOS+PholTMS) molar percentages and those after sulfonation, respectively.
Figure 4B:
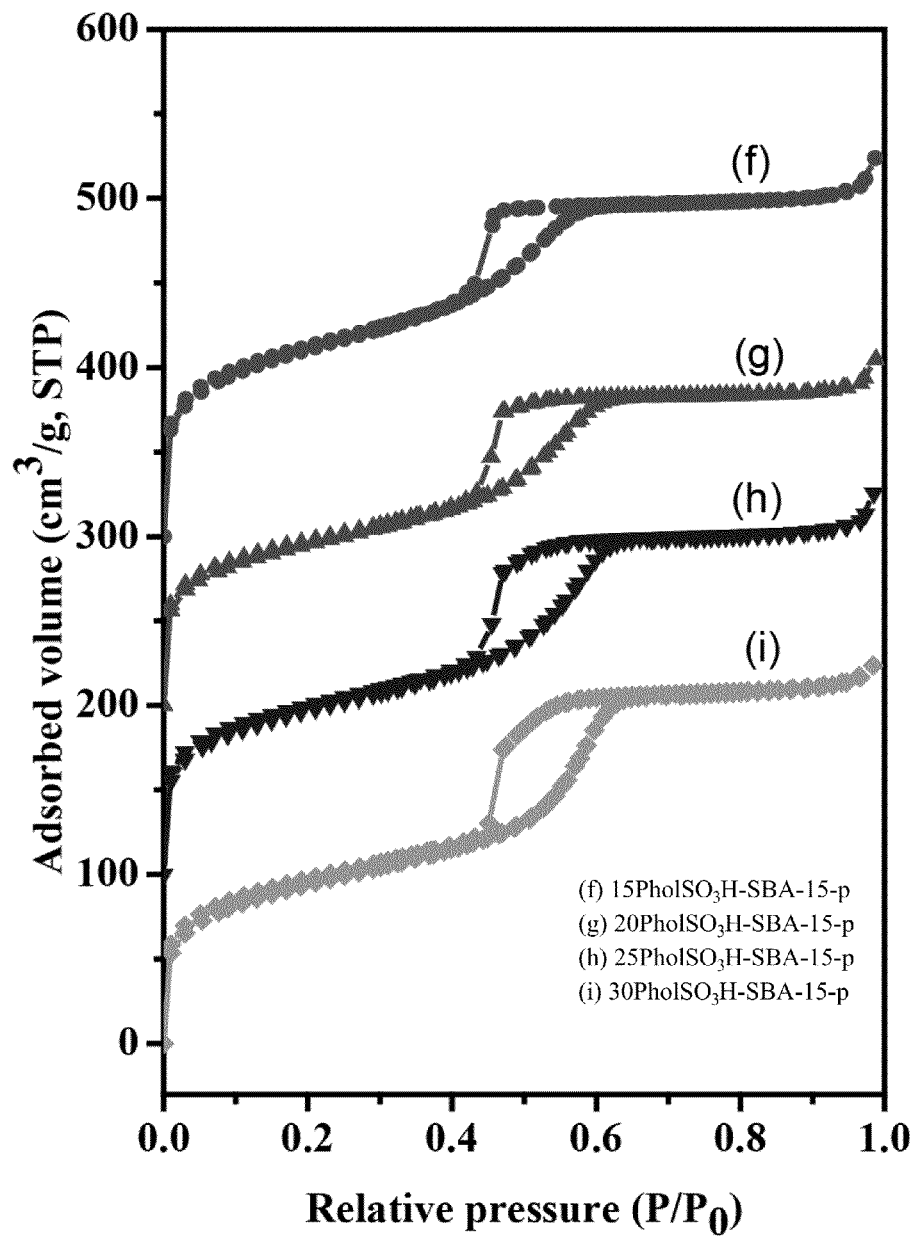

[a]Functional group content
[b]Determined by HC elemental analysis
[c]Determined by HCS elemental analysis
[d]Calculated by Brunauer-Emmett-Teller (BET) method in the P/P$_0$ range around 0.05-0.25
[e]Determined by Barrett-Joyner-Halenda (BJH) method using the N$_2$ desorption isotherms
[f]Determined by Barrett-Joyner-Halenda (BJH) method using the N$_2$ desorption isotherms FIGS. 3A and 3B are the small-angle XRD patterns of ethanol extracted xPhol-SBA-15-p and xPholSO$_3$H-SBA-15-p materials prepared with various PholTMS/(TEOS+PholTMS) molar percentages and those after sulfonation, respectively. In FIG. 3A, three well-resolved diffraction peaks corresponding to the (100), (110) and (200) planes of 2D-hexagonal p6mm pore structure are observed on xPhol-SBA-15-p materials, especially those of low PholTMS contents. However, in FIG. 3B, these diffraction peaks are almost disappeared after sulfonation reaction. This phenomenon suggested that the ordered pore structure is no longer present after treating the porous materials in sulfonic acid of such a high concentration.

FIGS. 3A and 3B are the small-angle XRD patterns of ethanol extracted xPhol-SBA-15-p and xPholSO$_3$H-SBA-15-p materials prepared with various PholTMS/(TEOS+

PholTMS) molar percentages and those after sulfonation, respectively. In FIG. 3A, three well-resolved diffraction peaks corresponding to the (100), (110) and (200) planes of 2D-hexagonal p6mm pore structure are observed on xPhol-SBA-15-p materials, especially those of low PholTMS contents. However, in FIG. 3B, these diffraction peaks are almost disappeared after sulfonation reaction. This phenomenon suggested that the ordered pore structure is no longer present after treating the porous materials in sulfonic acid of such a high concentration.

Example 6

Thienylsulfonic Acid-Functionalized SBA-15

In this embodiment, ThioTMS was co-condensed with a silica source to form thienyl-functionalized platelet SBA-15, which is denoted by Thio-SBA-15-p. Then, thienyl-functionalized platelet SBA-15 was sulfonated by concentrated $H_2SO_4$ to form thienylsulfonic acid-functionalized platelet SBA-15, which is denoted by $ThioSO_3H$-SBA-15-p.

The preparation conditions are similar to those of phenolsulfonic acid-functionalized platelet SBA-15, except that the PholTMS was replaced by ThioTMS. Therefore, the preparation details of $ThioSO_3H$-SBA-15-p are omitted here. In addition, thienyl-functionalized platelet SBA-15 are abbreviated as xThio-SBA-15-p, where "x" represents the ThioTMS/(TEOS+ThioTMS) molar percentage in the synthesis gels and "p" indicates the platelet morphology. The corresponding thienylsulfonic acid-functionalized platelet SBA-15 materials are abbreviated as $xThioSO_3H$-SBA-15-p.

Some physical properties of 15Thio-SBA-15-p and $15ThioSO_3H$-SBA-15-p are shown in Table 4. The S content of $15ThioSO_3H$-SBA-15-p is almost doubled after sulfonation. This implied that each thienyl group undergoes substitution of one sulfonyl acid group. On the other hand, the BET surface area, total pore volume and pore diameter decrease after the incorporation of thienyl moieties, and they were further decreased after sulfonation reaction.

TABLE 4

Some physical properties of SBA-15-p, 15Thio-SBA-15-p and 15ThioSO₃H-SBA-15-p

| Sample | S/Si (molar ratio) | | $S_{BET}$[c] (m²/g) | $V_{Total}$[d] (cm³/g) | $\phi_P$[e] (nm) |
|---|---|---|---|---|---|
| | gel[a] | solid[b] | | | |
| SBA-15-p | 0 | — | 823 | 0.98 | 7.0 |
| 15Thio-SBA-15-p | 0.15 | 0.10 | 513 | 0.65 | 5.2 |
| 15ThioSO₃H-SBA-15-p | — | 0.22 | 362 | 0.32 | 3.2 |

Figure 5:
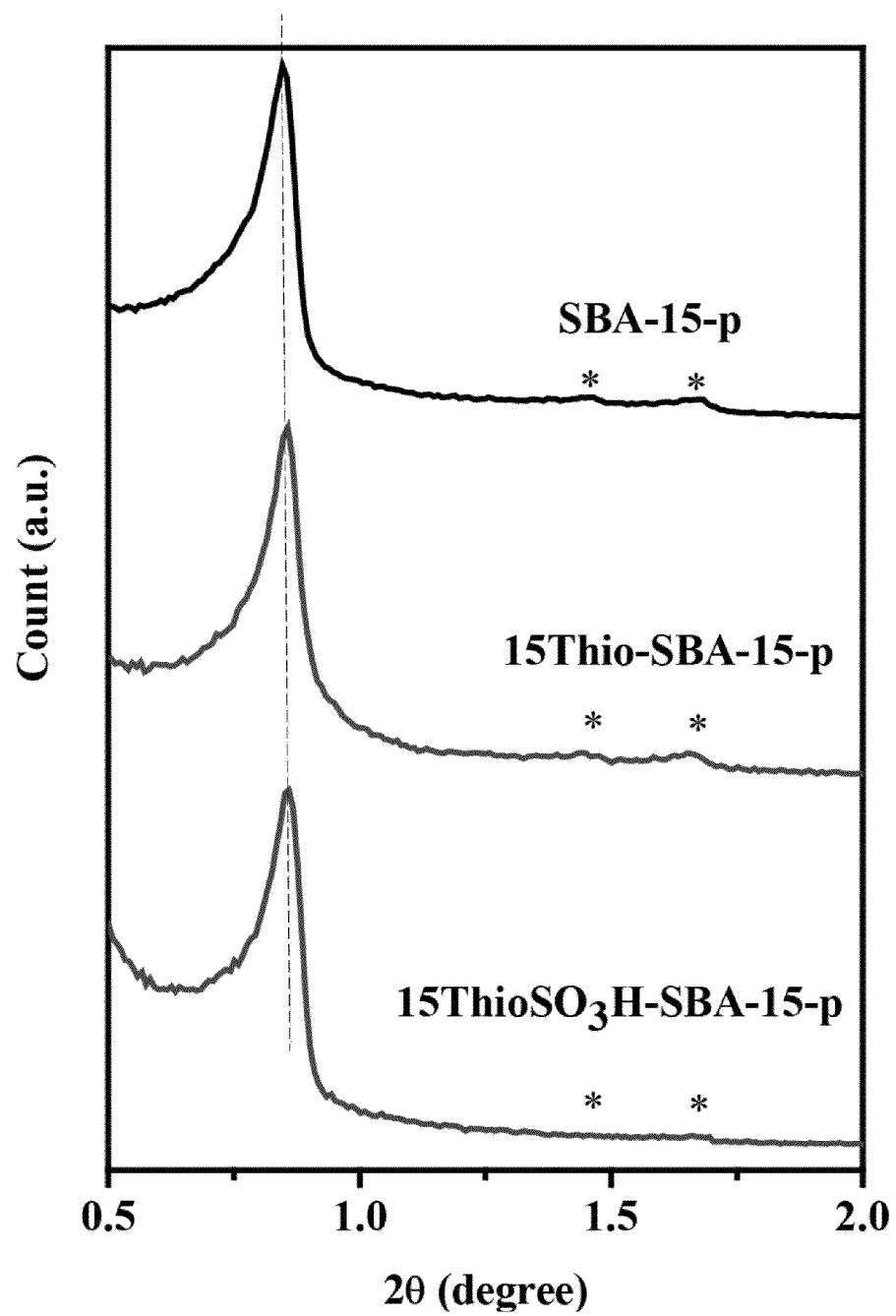
FIG. 5 shows XRD patterns of SBA-15-p, 15Thio-SBA-15-p and $15ThioSO_3H$-SBA-15-p.

[a]S content in the synthesis gel
[b]Determined by CHS elemental analysis
[c]Calculated by Brunauer-Emmett-Teller (BET) method in the P/P₀ range around 0.05-0.25
[d]Determined by Barrett-Joyner-Halenda (BJH) method using the N₂ desorption isotherms
[e]Determined by Barrett-Joyner-Halenda (BJH) method using the N₂ desorption isotherms FIG. 5 shows XRD patterns of SBA-15-p, 15Thio-SBA-15-p and $15ThioSO_3H$-SBA-15-p. In FIG. 5, three well-resolved diffraction peaks corresponding to the (100), (110) and (200) planes of 2D-hexagonal p6mm pore structure are observed for SBA-15-p and 15Thio-SBA-15-p, but the (110) and (200) peaks are hardly seen for $15ThioSO_3H$-SBA-15.

Figure 6:
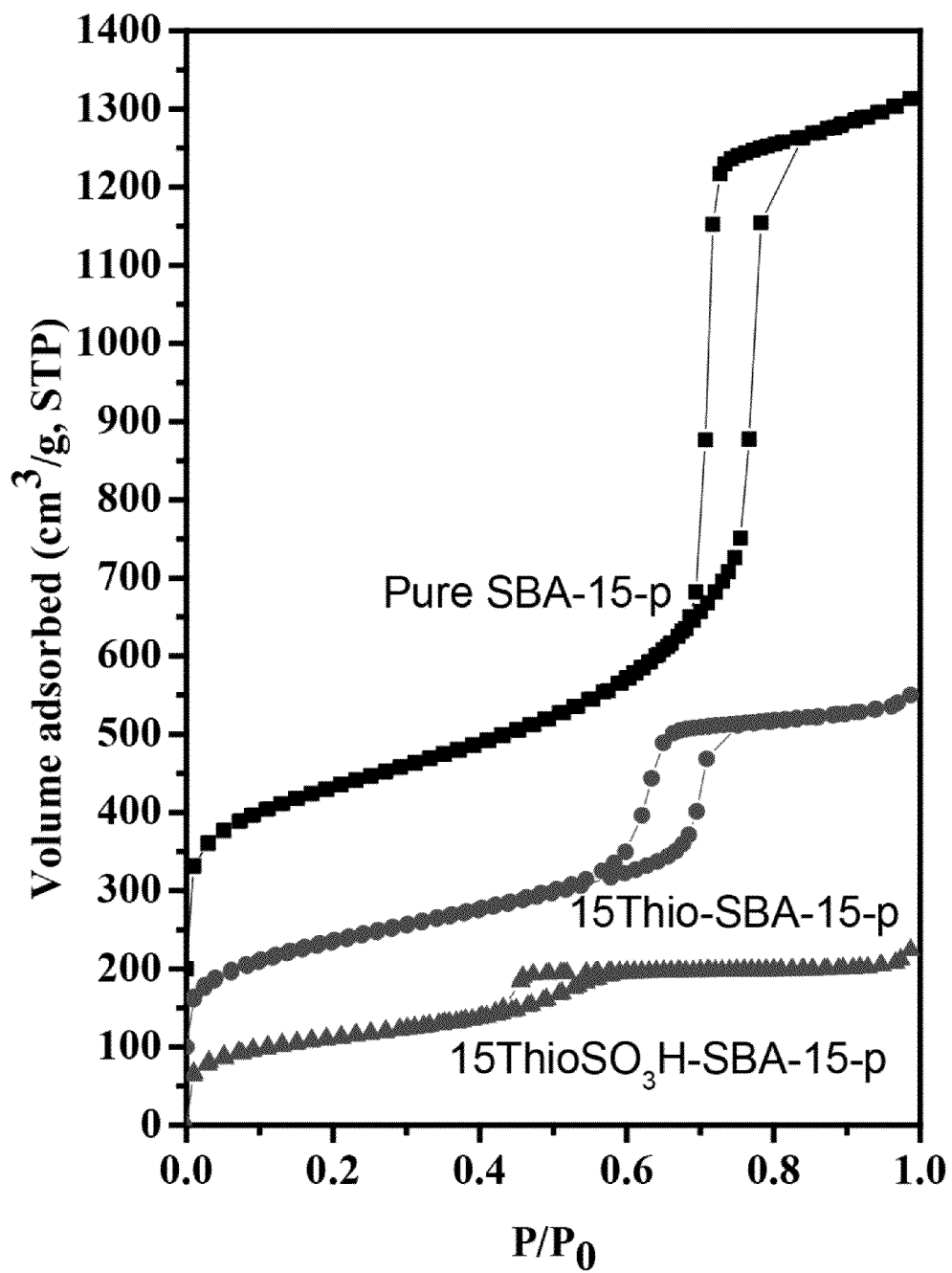
FIG. 6 shows the nitrogen adsorption-desorption isotherms of SBA-15-p, ethanol extracted 15Thio-SBA-15-p and dried $15ThioSO_3H$-SBA-15-p samples.

FIG. 6 shows the nitrogen adsorption-desorption isotherms of SBA-15-p, ethanol extracted 15Thio-SBA-15-p and dried $15ThioSO_3H$-SBA-15-p samples. In comparison to that of siliceous SBA-15-p, the hysteresis loops of functional materials shifted toward lower P/P₀ region. This implied that the pore diameter decreased as organic moieties were incorporated on the pore walls. On the other hand, the sulfonated material has a very small hysteresis loop, indicating that the channeling pores are partially obstructed.

Esterification of Palmitic Acid

Biodiesel refers to a vegetable oil- or animal fat-based diesel fuel consisting of long-chain alkyl (methyl, ethyl, or propyl) esters, and is typically made by chemically reacting lipids (e.g., vegetable oil, animal fat) with a short-chain alcohol producing fatty acid esters. At present, recycled frying oil is used as the source of oil to react with cheap methanol or isopropanol to produce biodiesel. However, large amount of free fatty acids in the recycled frying oil often poison the base catalyst used. Therefore, an acid catalyst has to be used first to pre-treat the recycled frying oil to lower the amount of the free fatty acid in the recycled frying oil. Industry even hope that a strong acid can be use to catalyze the transesterification reaction to simplify the preparation process.

Accordingly, the aryl sulfonic acid-functionalized solid prepared above are used to catalyze the esterification of palmitic acid (PA) with methanol (MeOH) or iso-propanol (iPrOH) to test the catalytic activity of the aryl sulfonic acid-functionalized solid prepared above.

Example 7

PholSO₃H-SBA-15 Catalyzed Esterification of Palmitic Acid

The phenolsulfonic acid-functionalized SBA-15 (15PholSO₃H-SBA-15-p) was used as the solid acid catalyst in the liquid phase esterification of palmitic acid (PA) with methanol (MeOH) and iso-propanol (iPrOH) to form methylpalmitate and iso-propylpalmitate as the products, respectively. The reactions were carried out at the reflux temperatures of the alcohols. The esters were found to be the only products in the present reaction condition based on the GC and GC-MS analyses.

Figure 7A:
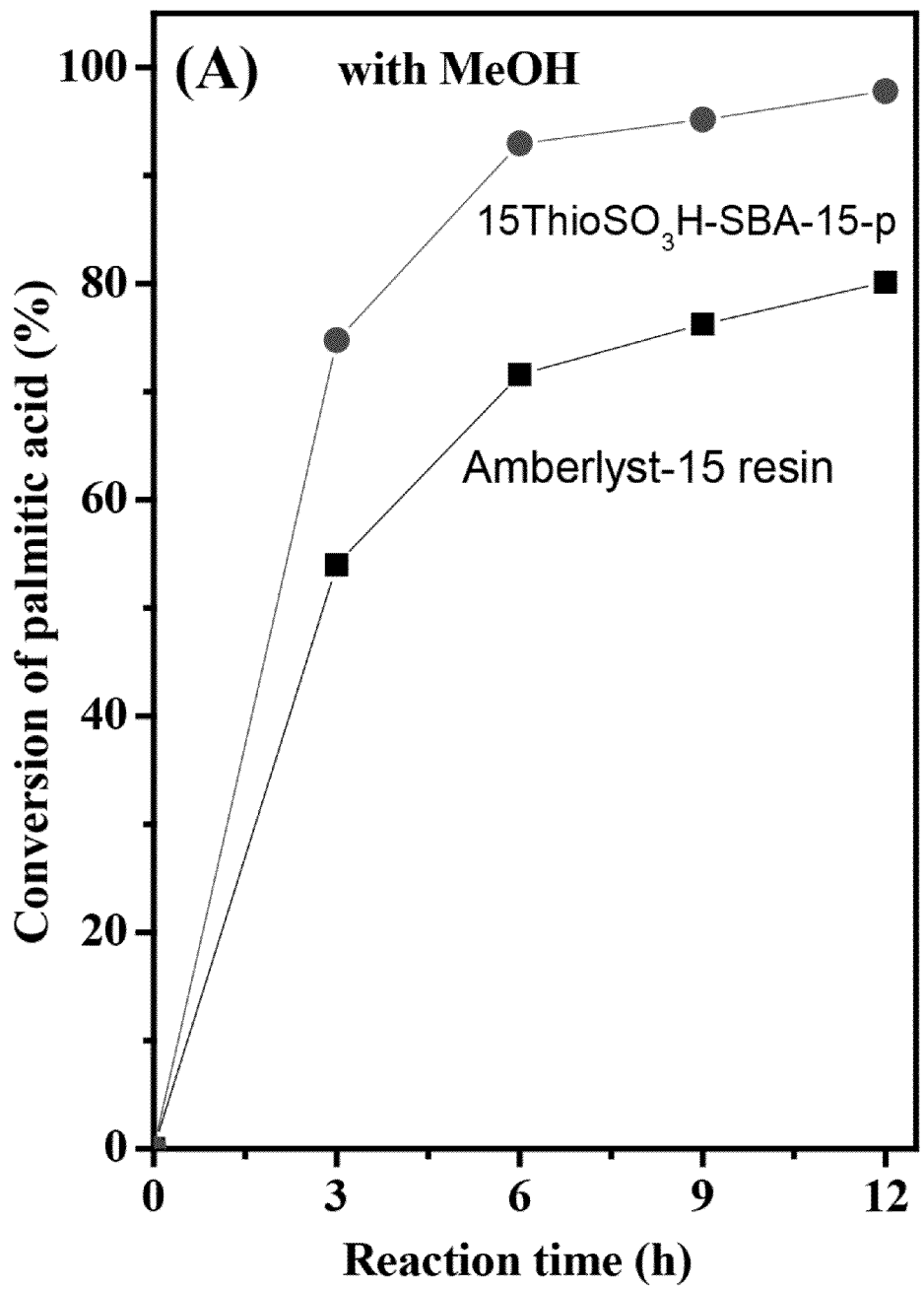
FIG. 7A and FIG. 7B show the conversions of palmitic acid in the esterification of palmitic acid with MeOH and iPrOH, respectively.
Figure 7B:
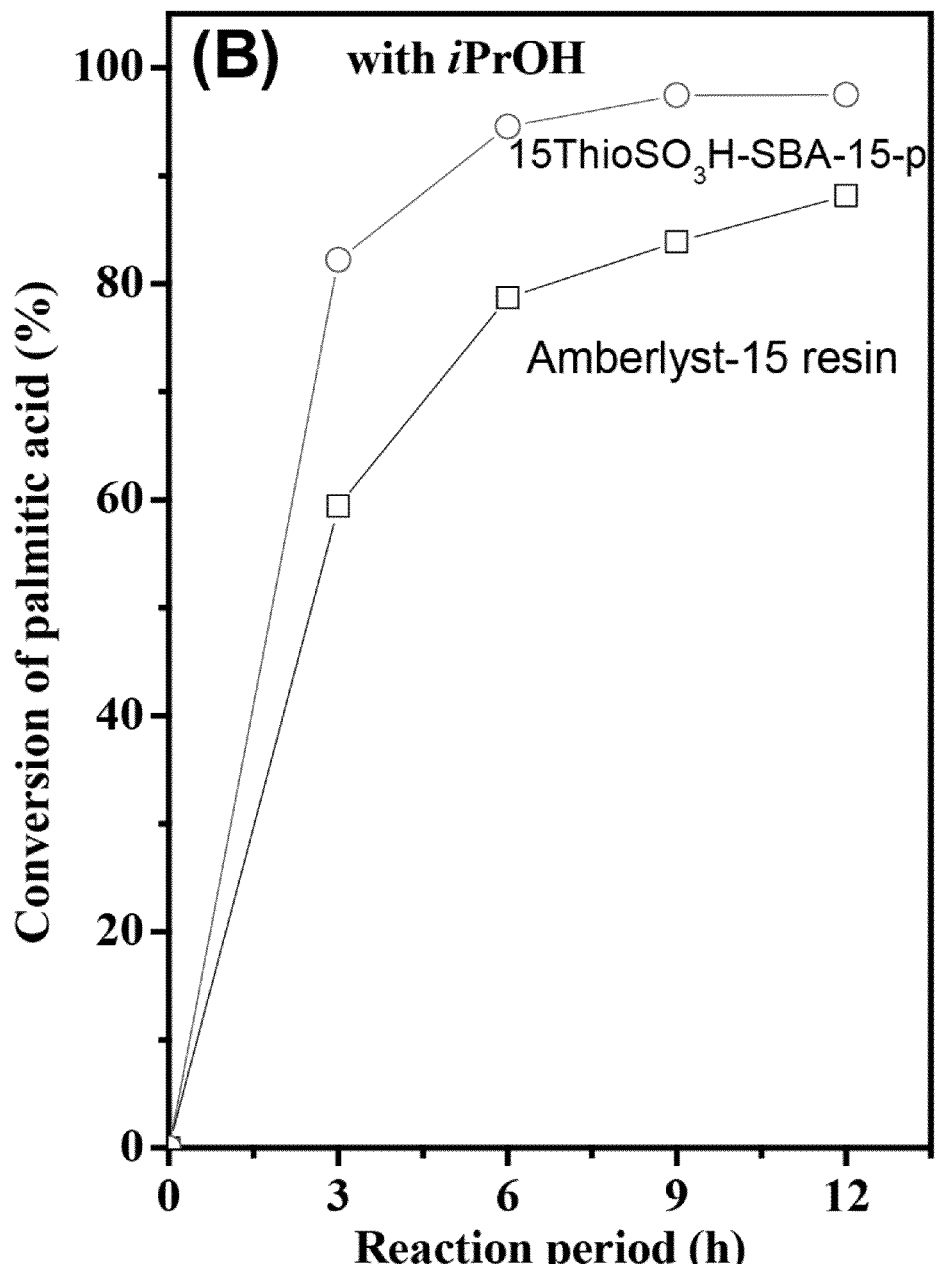

FIG. 7A and FIG. 7B show the conversions of palmitic acid in the esterification of palmitic acid with MeOH and iPrOH, respectively. In FIGS. 7A and 7B, the conversions of palmitic acid are shown as a function of reaction period over 15PholSO₃H-SBA-15-p and commercially available Amberlyst-15 resin. It is clearly shown that the conversions of palmitic acid over 15PholSO₃H-SBA-15-p increase much faster than those over Amberlyst-15 resin. After 12 hours reaction, significantly larger amounts of esters are obtained over 15PholSO₃H-SBA-15-p than Amberlyst-15 resin.

Table 5 demonstrates the recyclability of the 15PholSO₃H-SBA-15-p catalyst. The used catalyst was regenerated by simple filtration and drying at 100° C. The catalytic activities of 15PholSO₃H-SBA-15-p were well retained in comparison to that of the fresh catalyst after recycling for two times.

TABLE 5

Recyclability of the 15PholSO₃H-SBA-15-p catalyst

| Number of recycling[a] | Conversion of palmitic acid (PA) at 3 h (%) | |
|---|---|---|
| | with methanol | with iso-propanol |
| Fresh | 74.7 | 82.2 |
| 1st | 73.3 | 81.0 |
| 2nd | 73.1 | 81.3 |

[a]Recycling the catalyst after 24 h catalytic reaction

Figure 8A:
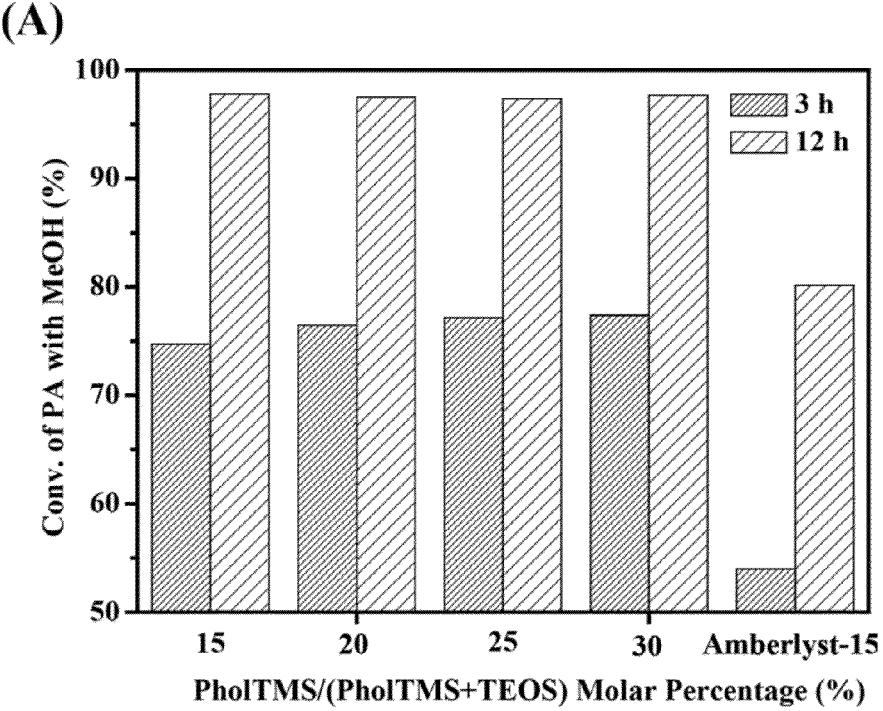
FIGS. 8A and 8B show the catalytic activities of SBA-15 functionalized with various amounts of phenolsulfonic acid ($xPholSO_3H$-SBA-15-p, x=15, 20, 25, 30) in the liquid phase esterification of palmitic acid (PA) with methanol (MeOH) and iso-propanol (iPrOH) to form methylpalmitate and iso-propylpalmitate as the products, respectively.
Figure 8B:
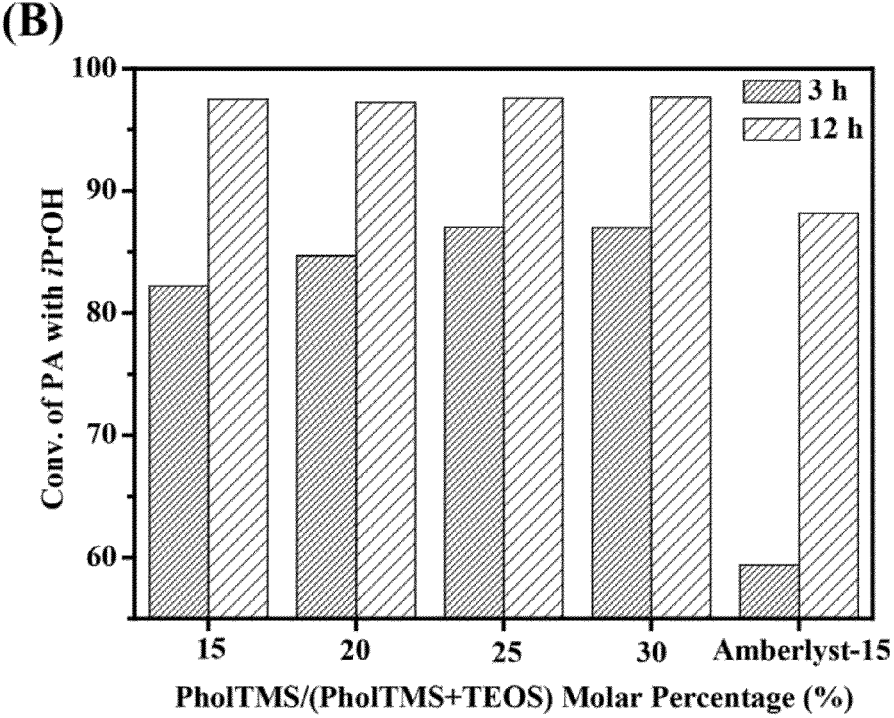

FIGS. 8A and 8B show the catalytic activities of SBA-15 functionalized with various amounts of phenolsulfonic acid (xPholSO₃H-SBA-15-p, x=15, 20, 25, 30) in the liquid phase esterification of palmitic acid (PA) with methanol (MeOH) and iso-propanol (iPrOH) to form methylpalmitate and iso-propylpalmitate as the products, respectively. The conversions of PA at 3 h and 12 h reaction period over PholSO$_3$H-SBA-15-p are compared with that over commercially available Amberlyst-15 resin.

FIGS. 8A and 8B show that the conversions of PA over xPholSO$_3$H-SBA-15-p at 3 h increase slightly with the increase of the phenolsulfonic acid loadings, and reach equilibrium after 12 h. The conversions of PA in esterification with iPrOH in FIG. 8B are higher than those with MeOH in FIG. 8A due to higher reflux temperature of iPrOH than MeOH. Nevertheless, the conversions of PA are much lower over Amberlyst-15 resin than over the functionalized SBA-15. After 12 h reaction, significantly larger amounts of esters are obtained over xPholSO$_3$H-SBA-15-p than Amberlyst-15 resin.

Example 8

ThioSO$_3$H-SBA Catalyzed Esterification of Palmitic Acid

The thienylsulfonic acid-functionalized SBA-15 (15ThioSO$_3$H-SBA-15-p) was used as the solid acid catalyst in the liquid phase esterification of palmitic acid (PA) with methanol (MeOH) to form methylpalmitate. The reaction was carried out at the reflux temperature of MeOH.

Figure 9:
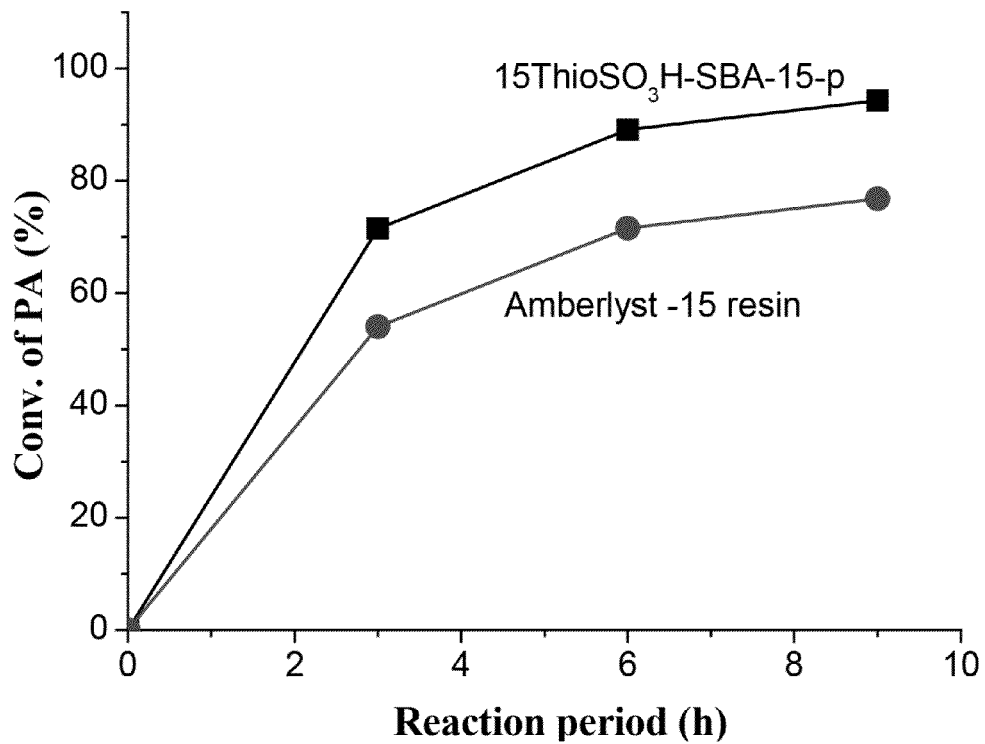
FIG. 9 shows the conversion of palmitic acid as a function of reaction period over $15ThioSO_3H$-SBA-15-p, in comparison to that over commercially available Amberlyst-15 resin.

FIG. 9 shows the conversion of palmitic acid as a functional of reaction period over 15ThioSO$_3$H-SBA-15-p, in comparison to that over commercially available Amberlyst-15 resin. It is clearly shown that the conversion of palmitic acid over 15ThioSO$_3$H-SBA-15-p increases much faster than that over Amberlyst-15 resin. After 9 hours reaction, significantly larger amounts of esters are obtained over 15ThioSO$_3$H-SBA-15-p than Amberlyst-15 resin.

Figure 10:
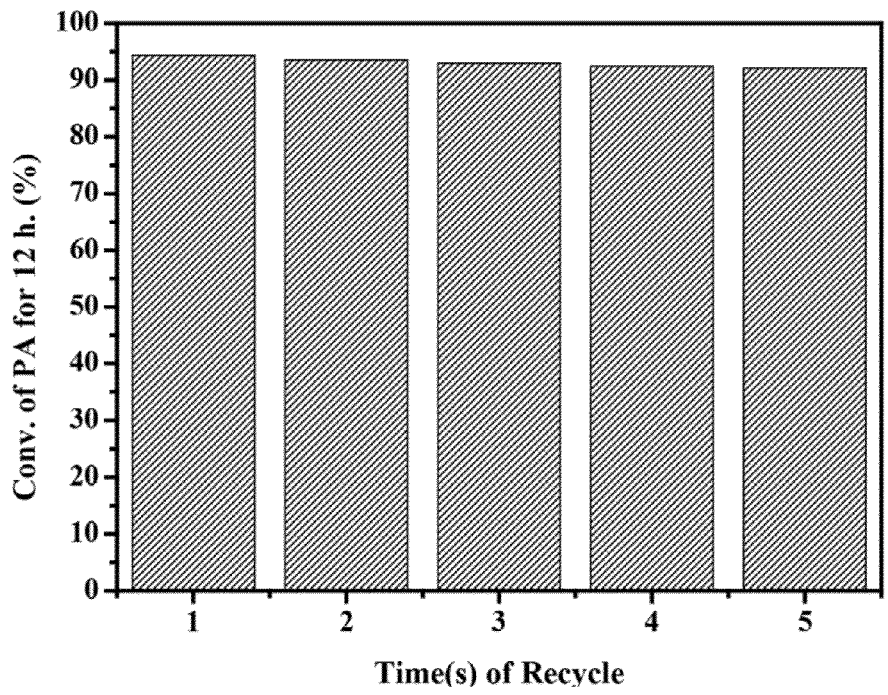
FIG. 10 demonstrates the recyclability of the 15ThioSO$_3$H-SBA-15-p catalyst.

FIG. 10 demonstrates the recyclability of the 15ThioSO$_3$H-SBA-15-p catalyst. Liquid phase esterification of palmitic acid (PA) with methanol (MeOH) was carried out for 24 hours before the catalyst was separated by filtration and drying at 100° C. The recycled catalyst was introduced to a new batch of reactants and the reaction proceeded at the same condition as that of the fresh catalyst. The conversions at 12th hour were recorded and shown in FIG. 10. There are negligible losses of catalytic activities after five times of recycles.

Example 9

PholSO$_3$H—ZrO$_2$ and SO$_3$H—ZrO$_2$ Catalyzed Esterification of Palmitic Acid The ZrO$_2$ materials functionalized with sulfonic acid and phenolsulfonic acid groups were used as the solid acid catalysts in the liquid phase esterifications of palmitic acid (PA) with MeOH. The reactions were carried out at the reflux temperature of MeOH. Methyl palmitate was obtained as the only product in the present reaction condition based on the GC and GC-MS analyses. The esterification of palmitic acid (PA) with MeOH was carried out at 60° C. in order to totally dissolve PA in the reaction mixture.

Figure 11:
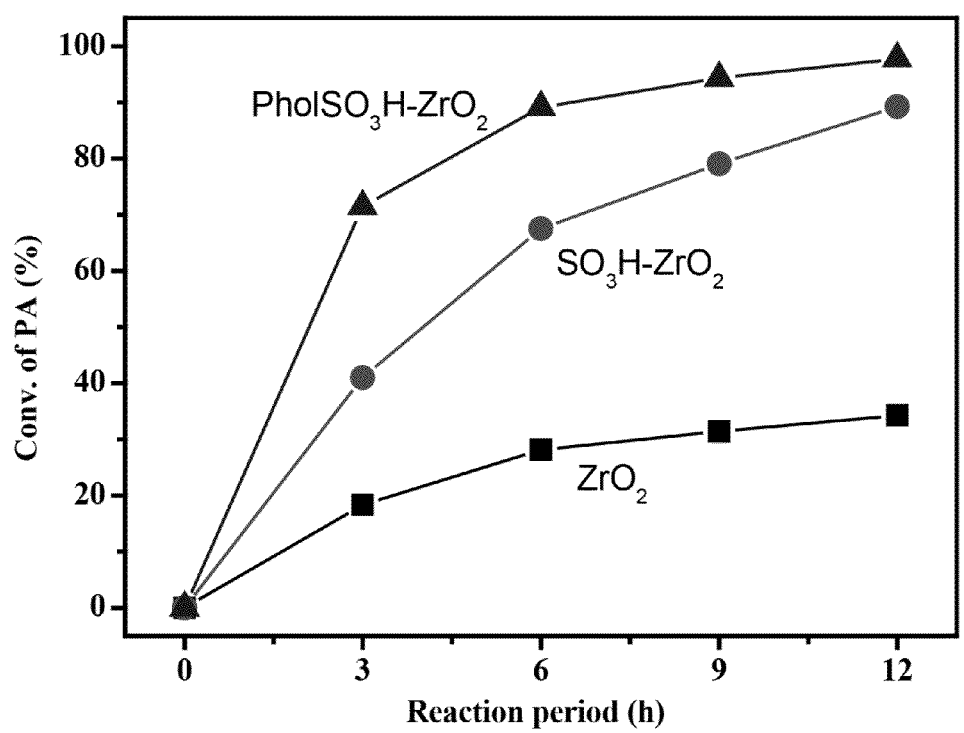
FIG. 11 shows the esterification of palmitic acid with methanol over ZrO$_2$, SO$_3$H—ZrO$_2$, and PholSO$_3$H—ZrO$_2$.

FIG. 11 shows the esterifications of palmitic acid with methanol over ZrO$_2$, SO$_3$H—ZrO$_2$, and PholSO$_3$H—ZrO$_2$. It is clearly shown that the esterification rates of palmitic acid with methanol over PholSO$_3$H—ZrO$_2$ are faster than those over ZrO$_2$ and SO$_3$H—ZrO$_2$.

Example 10

Various Phenolsulfonic Acid-Functionalized Solids Catalyzed Esterification of Palmitic Acid The phenolsulfonic acid-functionalized on different solid supports were used as the catalysts in the liquid phase esterification of palmitic acid (PA) with MeOH and iPrOH to form methylpalmitate and iso-propylpalmitate as the products, respectively. The reactions were carried out at the reflux temperature of MeOH.

Figure 12A:
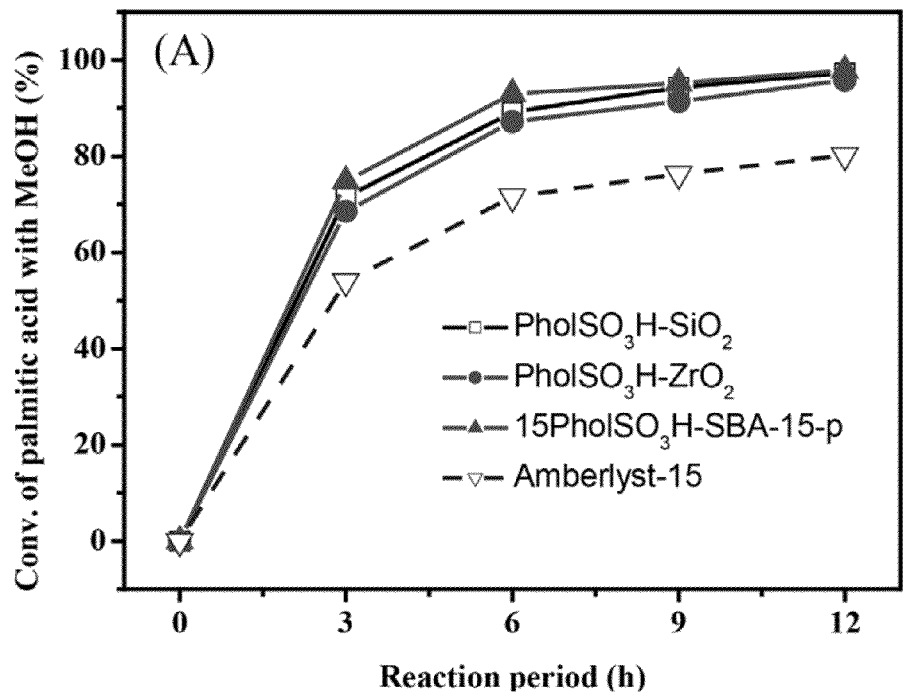
FIGS. 12A and 12B show the conversions of palmitic acid over different solid acid catalysts in the esterification of palmitic acid with MeOH and iPrOH, respectively.
Figure 12B:
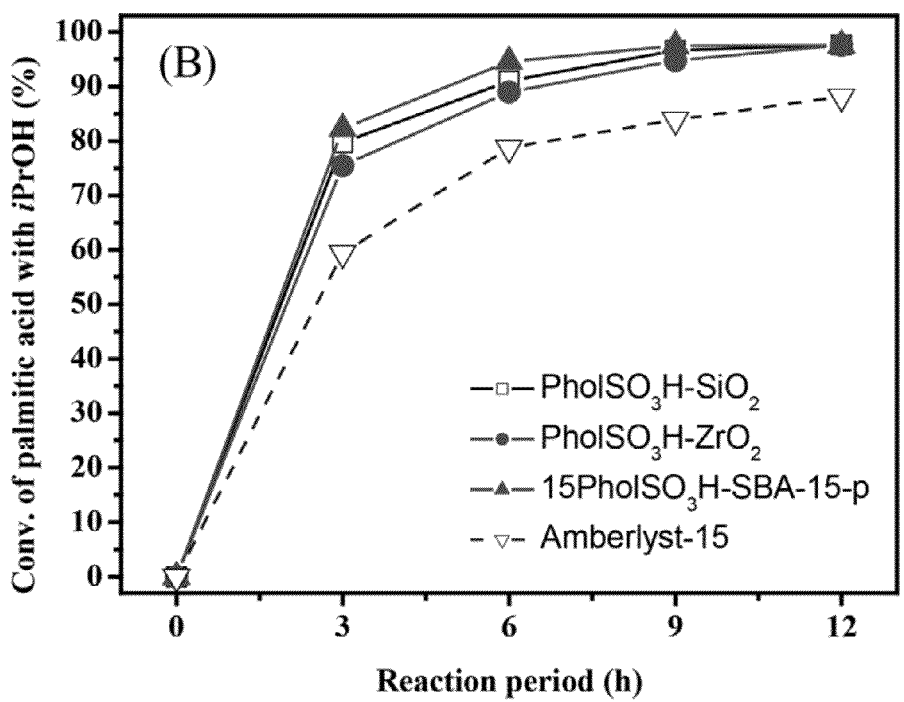

FIG. 12A and FIG. 12B show the conversions of palmitic acid in the esterification of palmitic acid with MeOH and iPrOH, respectively. In FIGS. 12A and 12B, the conversions of palmitic acid are shown as a function of reaction period over different phenolsulfonic acid-functionalized solids, in comparison to that over commercially available Amberlyst-15 resin. It is clearly shown that the conversions of palmitic acid over phenolsulfonic acid-functionalized solids increase much faster than those over Amberlyst-15 resin. After 12 hours reaction, significantly larger amounts of esters are obtained over phenolsulfonic acid-functionalized solids than those over Amberlyst-15 resin.

Among the three phenolsulfonic acid-functionalized solids, 15PholSO$_3$H-SBA-15-p prepared by co-condensation gives slightly higher conversions than phenolsulfonic acid-functionalized silica gel and zirconia, both are prepared by grafting methods. Nevertheless, the conversions of palmitic acid after 12 hours are very similar for these three phenolsulfonic acid-functionalized solids.

Accordingly, various aryl sulfonic acid-functionalized solids were prepared above. The catalytic activity of the prepared aryl sulfonic acid-functionalized solids was also test, and it showed that the catalytic activity was better than commercialize Amberlyst-15 resin. This result shows that the prepared aryl sulfonic acid-functionalized solids are suitable to be used as a strong solid acid.

All the features disclosed in this specification (including any accompanying claims, abstract, and drawings) may be replaced by alternative features serving the same, equivalent or similar purpose, unless expressly stated otherwise. Thus, each feature disclosed is one example only of a generic series of equivalent or similar features.

What is claimed is:

1. A method of preparing an aryl sulfonic acid-functionalized solid, comprising:
    forming a 3-arylpropyl trimethoxysilane by reacting 3-chloropropyl trimethoxysilane with an aromatic compound;
    forming an aryl-functionalized solid by grafting the 3-arylpropyl trimethoxysilane onto an inorganic solid material having free —OH groups thereon in an organic solvent under a reflux condition; and
    forming an aryl sulfonic acid-functionalized solid by sulfonating the aryl-functionalized solid by a sulfonating agent.

2. The method of claim 1, wherein the aromatic compound is phenol, alkyl phenol, thiophene, or alkyl thiophene.

3. The method of claim 1, wherein the inorganic solid material is silica gel, porous silica, or Zr(OH)$_4$ powders.

4. The method of claim 1, wherein the organic solvent is toluene, xylene, ethylbenzene, or octane.

5. The method of claim 1, wherein the aryl-functionalized solid is sulfonated at 60-90° C. for 6-36 hours.

6. The method of claim 1, wherein the sulfonating agent is concentrated sulfuric acid, a mixture of oleum and concentrated sulfuric acid, or $SO_2Cl_2$.

\* \* \* \* \*